United States Patent

Webb et al.

[11] Patent Number: 5,531,667
[45] Date of Patent: Jul. 2, 1996

[54] ORTHOPAEDIC CASTING BANDAGES

[75] Inventors: Julian A. Webb, Clifton; Patrick L. Blott, York, both of United Kingdom

[73] Assignee: Smith & Nephew plc, London, England

[21] Appl. No.: 197,823

[22] Filed: Feb. 17, 1994

[30]    Foreign Application Priority Data

Feb. 17, 1993  [GB]  United Kingdom .................... 9303200

[51] Int. Cl.⁶ ........................................................ A61F 5/00
[52] U.S. Cl. ..................... 602/8; 602/6; 602/41; 602/63
[58] Field of Search ..................... 602/1, 5, 6, 8, 602/12, 26, 27, 63, 75, 76, 41, 60, 900

[56]               References Cited

U.S. PATENT DOCUMENTS 2,574,873  11/1951  Jobst .......................................... 602/63
3,923,049  12/1975  Lauber et al. .......................... 128/91 R
4,632,106  12/1986  Gumm .................................... 128/165
4,798,200   1/1989  Warthen et al. ........................... 128/89
4,856,502   8/1989  Ersfeld et al. ............................. 128/90

FOREIGN PATENT DOCUMENTS

WO90/14060  11/1990  European Pat. Off. .

Primary Examiner—Corrine M. McDermott
Attorney, Agent, or Firm—Larson and Taylor

[57]                ABSTRACT

A plurality of layers of a bandage can be jointed together at edges thereof to provide a casting bandage, which can then be coated/impregnated with a resin.

Desirably the layers are formed from tubular members which are edge-stitched together.

22 Claims, 1 Drawing Sheet

ORTHOPAEDIC CASTING BANDAGES

The present invention relates to orthopaedic tubular casting bandages, fabrics therefor, hardened casts therefrom and methods for the production thereof.

Casting or splinting bandages are commonly used in the treatment of bone fractures or deformities to provide a rigid or stiff immobilising or support orthopaedic cast on a body portion and in particular a body extremity such as a foot, leg, hand or arm. Casting bandages normally comprise a flexible woven or knitted substrate typically containing yarns of cellulosic, polyester, polypropylene or glass fibres in the form of a strip which carries a hardenable resin.

In use the strip bandage is applied by winding one or more strips around the affected body portion and allowing the resin to harden. The strength of the cast depends to some extent on the amount of resin, type of substrate and the number of substrate layers in the cast. Normally it is necessary to apply several layers of the casting bandage strip to obtain casts with good cast strength.

Casting bandages in tubular form have been proposed which advantageously allow the application of a casting bandage without the need to wind it around a body portion. International Patent Application No. WO90/14060 discloses a tubular casting bandage comprising a single bulky substrate layer carrying a hardenable resin which thus avoids the need to apply several layers of the bandage to form of a cast of adequate strength. The patent also discloses a composite or multilayer form of the bandage comprising an inner padding layer and optionally an outer substrate layer to hold in place a cuff formed by folding back an edge of the padding layer. WO90/14060 teaches that the composite or multilayer bandage can be assembled by mounting the inner tubular layer on a mandrel or plate and pulling the other tubular layers in successive operations over the inner layer. It has been found, however, that this method of assembling the tubular layers of a composite or multilayer casting bandage may be inconvenient or difficult to achieve for example when the tubular layers are in the form of continuous tubes and/or comprise substrate layers carrying an viscous or tacky resin.

Multilayer tubular casting bandages have now been found which can provide casts of good strength and which can be formed without having to resort to the difficult methods of assembly hereinabove described.

Accordingly the present invention provides a tubular orthopaedic casting bandage comprising a stack formed of a plurality of layers of material which are joined together at edges thereof, by zig-zag joining means such as zig-zag stitching wherein two adjacent layers define a sleeve for receiving a body member.

"Edge stitching" is used to refer to stitching provided at or proximal to opposed edges of the bandage (when the bandage is in flattened form so as to have first and second opposed longitudinal edges).

The bandage of the invention may comprise adjacent layers which are only attached to each other at opposed edges. The unattached portions of adjacent layers between the side joins can thus advantageously provide the bandage with one or more tubular regions or openings adapted to receive and fit around a body portion.

The casting bandage of the invention can be readily formed by edge-stitching together layers of a tubular material, layers of a sheet material (which may be planar or folded) or a mixture of both types of layer.

The tubular casting bandage of the present invention can thus avoid the need to assemble a multilayer construction by pulling successive tubular layers over or within an initial tubular layer.

The bandage of the present invention may comprise a hardenable material (e.g. a casting resin) which is preferably added to the inner and outer layers prior to forming the bandage.

Thus multilayer casts can be formed without the need to apply several tubular bandage substrates carrying a hardenable resin successively to a body portion.

The tubular bandage of the invention can be adapted in size to fit the body portion to which it is to be applied. The size will vary according to the size of a body portion such as an arm, leg or trunk.

The width of the tubular bandage in lay flat form for use on an adult arm can be suitably at least 3 cm and preferably at least 4 cm.

Similarly the width of the tubular bandage in lay flat form can be suitably less than 25 cm and preferably less than 20 cm.

Apt tubular bandages of the invention in lay flat form for use on an arm have a width of 5 to 15 cm.

The width of a tubular bandage of the invention can however vary from at least 1 cm for a finger more than 50 cm for trunk of the body.

The tubular bandage can have a uniform width along its length. However, the tubular may vary in width along its length for example to accommodate a tapered body portion.

The length of the tubular bandage can be adapted to fit the body portion to which it is to be applied.

The bandage of the invention is normally extensible in at least the width direction and possibly also the length direction thereof.

The bandage can suitably have an extension of at least 25%, more suitably at least 50%, favourably at least 75% and can preferably have an extension of at least 100% for example 100% to 200% in the width direction. The extension of the tubular bandage can be measured by a conventional bandage extension test in which the tubular bandage in lay flat form is extended widthwise to its maximum extent. In this test the original (Ow) and stretched width (Sw) are recorded. The extension of the bandage can then be expressed as a percentage of the original width using the formula extension $$\% = \frac{(Sw - Ow)}{Ow} \times 100$$

The extensible nature of the tubular bandage allows it to be applied to and to conform to a body portion such as a limb. Extensibility may be required in the lengthwise direction where the system is intended for use in bandaging regions such as the elbow, knee or ankle and heel. Bandages which have an extension in the length direction of 10% to 20% have been found suitable for such uses.

Desirably the bandage is elastically extensible in at least the width direction. Suitably the bandage will be sufficiently elastic to recover to at least 60% of its original dimensions preferably at least 80% when extended to 100% in the width direction.

The extensible nature of the tubular bandage of the invention renders it highly adaptable for application to a body portion.

The bandage comprises suitably at least three substrate layers, favourably at least four substrate layers and preferably at least six substrate layers. Similarly the bandage comprises suitably up to twenty substrate layers, favourably up to eighteen substrate layers and preferably up to 16 substrate layers. Apt bandages of the invention comprises four to sixteen substrate layers for example six to twelve substrate layers.

Reference to numbers of layers of the bandage of the present invention are based upon the total number of layers which would be sectioned through in a cross section through the whole bandage (i.e. not just a radial section). Since tubular members are sectioned through twice in such a cross section, they are taken as two layers. This also applied to sheets which have been folded in two.

The individual substrate layers within the bandage of the invention can have a number of different forms. For example, two substrate layers of the bandage can be formed from a sheet folded in two or from a tubular member (as indicated above). Three individual layers can be formed from a folded sheet having two folds, etc. Such multifolded layers can be aptly in the form of a zig-zag folded strip.

Alternatively the bandage of the invention can comprise two or more unfolded layers, for example, in the form of strips.

Favoured tubular bandages of the present invention comprise a plurality of tubular members.

Apt bandages of the invention comprise eight to twelve substrate layers in tubular form ie. four to six tubular members.

The width of the individual substrate layers in the bandage can be different but is preferably normally similar to that of each other and the width of the bandage. The width of inner or outer layers in relation to other layers however may be adapted to accommodate the tubular nature of the bandage of the invention.

When individual or sets of layers have a different width from other layers it is preferred that such layers are adapted for example by extension or compression so that all the superposed layers have a similar width.

Suitable fabrics for use as substrate layers in the tubular bandage of the invention include any of the widthwise extensible fabrics used as substrates in conventional casting bandages such as tubular or strip woven or knitted fabric substrates of which tubular knitted fabric substrates are preferred.

Suitable methods for producing knitted fabric substrate include those for making socks or stockinettes. Such methods include both weft and warp knitting methods and include knitting patterns such as rib or cable knitting, knitting with pillar stitches, knitting with crimped yarns or looped yarns for example "Terry" towelling and combinations of these knitting methods. The knitted fabric substrate however may advantageously contain holes or apertures in addition to the normal yarn interstices.

The size of the holes or apertures in individual substrate layers of the tubular fabric or bandage may be different. It is preferred, however, that the outer substrate layers of the tubular fabric have small apertures to provide a cast formed from the tubular bandage with a relatively smooth surface.

The yarns employed in the substrate fabrics can comprise the so called 'high tenacity yarns' which although they can be readily knitted, have a resistance to deformation and thus an 'apparent resilience'. A substrate fabric such as a tubular knitted fabric can comprise yarns of hydrophilic or hydrophobic fibres or a combination of these fibres. Suitable hydrophilic fibres include cellulosic fibres such as cotton, viscose or acetate rayon fibres. Preferred substrate fabrics comprise hydrophobic fibres. Suitable hydrophobic fibres include acrylic, polyester and polyolefine fibres such as high density polyethylene or polypropylene fibres. Other fibres such as polyamide fibres, however, may also be present in the bandage. Glass or carbon fibre may also be knitted up, for example by weft knitting to produce a suitable substrate.

Yarns suitable for use in the invention include polypropylene 420 denier/70 filament yarns such as those manufactured be Plasticizer Ltd., E-Glass fibres (50 Tex, 6 μm filament) yarn sold by Pittsburgh Plate Glass Company and 167 DECITEX filament Polyester yarn sold MOWBRAY.

Favoured tubular or strip knitted substrate fabrics used in the invention comprise yarns of hydrophobic fibres to render the substrate non-absorbent to water and aqueous fluids.

A substrate such as a tubular substrate used in the invention preferably also comprises an elastic component such as elastic yarn to render the layer elastically extensible in the width direction. The elastic extension of the substrate should be sufficient to permit elastic extension of the resin laden system within the aforementioned ranges.

The elastic yarn can be a mono or multifilament yarn of an elastomer such as rubber polyurethane for example Lycra or Spandex yarn or an A—B—A block copolymer for example styrene—butadiene—styrene copolymer sold under the Trade Mark CARIFLEX and styrene-ethylene-butylene-styrene polymers sold under the Trade Mark KRATON. The elastic component of such elastic yarns may be surrounded by sheath of a suitable material such as a polyamide, eg. Nylon. Suitable sheathed rubber based elastic yarns include yarns sold by Heathcotes Ltd. under the trade designations 'Fifties', 'Seventy fives' or 'Nineties' which are polyamide sheathed yarns containing respectively 50 and 75 rubber filaments per linear inch (2.54 cm). The elastic yarn can be attached to or included in a tubular knitted substrate layer as a component which extends in a circular or spiral manner around the circumference of the tube. Preferably the elastic yarn is included into the tube during the knitting process. Such knitting processes can be those conventionally used for making elastic tubular bandages or elastic stockings. Rubber filaments may be included, with advantage into glass fibre knitted substrates.

Other materials suitable for the substrate of a bandage include non-woven materials such as lofted non-woven fabrics (having fibres randomly orientated in all three dimensions) and foam materials.

Substrates comprising hydrophilic fibres may also be pretreated with a water-proofing agent to inhibit the substrate absorbing moisture.

A substrate for use in the invention which is to be used on the hand, wrist or lower arm may advantageously be coloured, for example patterned. Similarly, a substrate for a bandage which is to be used on the foot, ankle or lower leg may advantageously be coloured, for example patterned. One or more differently coloured materials such as yarns may be employed for the substrate for example a knitted substrate may be produced where different coloured yarns are employed to produce a pattern such as a tartan. Such coloured or patterned substrates in combination with a substantially transparent and colourless hardenable resin can provide a bandage cast which is not as conspicuous as a normal plaster cast and may render the cast more aesthetically acceptable.

The tubular cast bandage of the invention can advantageously comprise one or more other layers such as padding or barrier layers in addition to substrate layers. Such layers however should be extensible layers in the width direction to maintain the extensibility of the tubular bandage.

In favoured embodiments of the invention the tubular cast bandage or fabric of the invention comprises a pair of padding layers. Suitable padding layers can include any of the extensible padding materials conventional used under casting bandages. In preferred embodiments of the invention the pair of padding layers are in tubular form.

Suitable tubular padding is disclosed in European Patent Application No. 0356078 and International Patent Application No. WO90/14060 the disclosure of which is incorporated herein.

The padding layers for use in the invention can have widthwise extensibility which is similar to or greater than that of the tubular bandage of the invention. Favoured padding layers can also be elastically extensible in the width direction.

Favoured extensible tubular padding for use in the tubular bandage of the invention comprise a lofted non-woven fabric bonded to a tubular woven or knitted stockinette. Preferred padding layers of this type comprise an elastic yarn for example arranged in a radial or spiral manner in the stockinette.

The padding layers will normally be located within the bandage layers to provide the tubular opening in the bandage which is adapted to accommodate a body portion.

The padding layers can be located centrally or non-centrally within the substrate layers of the bandage. Padding layers located centrally within the substrate layers can provide a cast of uniform thickness around a body portion. Padding layers located non-centrally within the substrate layers can provide an asymmetrical cast. When the padding layers are located non-centrally to one side of the substrate layers, a slab cast can be formed.

A tubular bandage or fabric of the invention can also comprise a pair of barrier layers which are impermeable to liquids. The each barrier layers will normally be adjacent to a padding layer in the fabric or bandage to inhibit the liquid penetrating to a barrier layer.

In a tubular bandage of the invention the barrier layers can advantageously inhibit aqueous liquids such as water used to cure a water hardenable resin penetrating from the outside of the bandage to the padding layers.

A barrier layer for a tubular bandage can advantageously be moisture vapour permeable to allow the escape of moisture from under the cast.

Moisture vapour permeable and water impermeable layers may be provided by a water proofing agent or a water impervious layer on the padding layers.

Suitable waterproofing agents include non-toxic waterproofing agents used for textiles such as wax, silicone resin or fluorinated polymer waterproofing agent. Such agents: are normally available as a solution or dispersion.

Apt waterproofing agents are a wax waterproofing agents in emulsion form known as Nickwax TX10 available from Nickwax Ltd. and Super pel available from Grangers Ltd.

The padding layer may be treated for example by impregnation to provide the waterproof agent throughout the thickness of the fabric. Alternatively the non-woven fabric may be treated, for example by coating, to provide the waterproof agent at a surface layer of the fabric.

Suitable waiter vapour permeable, water impervious layers for the bandage can comprise a water insoluble polymer which is preferably also an elastomer to render the layer elastic and conformable.

Such layers can be continuous, voided or microporous.

Favoured elastomeric moisture vapour permeable layers include those formed from polyether polyurethane, polyester polyurethane, hydrophilic polyurethane and polyether-polyamide and polyester-polyether copolymers.

Suitable polyether polyurethanes are described in U.S. Pat. No. 2,899,411. Suitable polyester polyurethanes are described in U.S. Pat. No. 2,871,218. Apt polyester and polyether polyurethanes are known as Estane (Trade Mark) available from B. F. Goodrich and in particular grades 5701, 5702, 5703, 5714F and 580201.

An apt polyester-polyether copolymer is known as Hytrel 4056 available from Dupont.

An apt polyether-polyamide copolymer is known as Pebax 2533 or 4033 available from AtO Chemicals.

Suitable hydrophilic polyurethane layers for use in the inventions are disclosed in European Patent No. 91800.

The weight per unit area of the layers used as the barrier layers can suitably be 5 to 80 $g/m^2$, more suitably 5 to 50 $g/m^2$ and can preferably be 7 to 30 $g/m^2$ for example 10 $g/m^2$.

Moisture vapour permeable barrier layers used in the invention can suitably have a moisture vapour transmission rate of at least 1000 $g/m^2/24$ h, more suitably at least 2000 $g/m^2/24$ h and preferably at least 5000 $g/m^2/24$ h at 37° C. at 100% to 10% relative humidity difference. The moisture vapour transmission rate of a non-woven fabric can be readily determined by the Payne Cup Method (in the upright position) described in European Patent No. 46071.

Similar barrier layers to that in the bandage may be present in a tubular fabric of the invention to inhibit penetration of resin into the padding layers.

Suitable barrier layers for tubular fabric may be temporary layers which can be removed after impregnation of the fabric or during curing of the bandage for example by dissolution in the water used to cure the resin.

The tubular bandage of the invention may comprise a hardenable resin carried on the substrate layer. The resin can be any suitable hardenable resin for orthopaedic cast bandages. Suitable hardenable resins include water hardenable or actinic radiation (visible or UV) activated hardenable resins. Favoured hardenable resins are water hardenable resins including polyurethane or acrylic prepolymer hardenable resins.

Suitable prepolymer resins of this type can be selected from those conventionally used for orthopaedic casts. Preferred hardenable resins, however, are polyurethane prepolymer resins. Such resins are typically reaction products of a polyisocyanate and a polyol such as a polyether diol optionally containing a triol. These resins may contain a catalyst such as a tertiary amine and/or a stabiliser such as an acidic material. Preferred catalysts are dimorpholino diethylether and bis(2,6-dimorpholino) diethylether. preferred stabilisers are methane sulphonic acid and succinic anhydride.

Suitable water hardenable polyurethane prepolymer resins containing catalysts and/or stabilisers of this type are disclosed in International Patent Application No. 86/01397, U.S. Pat. No. 4,433,680 and United Kingdom Patent No. 2,196,944 the disclosure of which is incorporated herein by reference. Other resins suitable for use in the present invention include those described in International Publication No. WO89/08463 and in British Patent Specification No. 2207141.

The tubular casting bandage of the invention comprises a plurality of substrate layers and therefore the amount or hardenable resin which may be carried by these substrate layers will generally be greater than that of a conventional casting bandage comprising a single substrate layer.

The amount of hardenable resin in a tubular casting bandage of the invention can be suitably more than 40% by weight preferably more than 50% by weight of the weight of the substrate layers. Similarly the amount of hardenable resin in a tubular casting bandage can be suitably less than 80% by weight and preferably 70% by weight of the weight of the substrate layers.

The amount of hardenable resin in apt tubular casting bandages of the invention is 50% to 70% by weight for example 55 to 65% by weight of the weight of the substrate layers.

The total weight per unit area of hardenable resin on the substrate layers of the bandage can be 1000 gm$^2$ favourably more than 2000 gm$^2$ and preferably more than 3000 gm$^2$. Similarly the total weight per unit area of hardenable resin on the substrate layers of the bandage can be suitably less than 10000 gm$^2$, favourably less than 9000 gm$^2$ and preferably less than 8000 gm$^2$.

The total weight per unit area of hardenable resin on the substrate layers of apt tubular bandages of the invention is 3000 to 8000 gm$^2$.

The tubular bandages of the invention have a tubular opening, adapted to fit a body portion located centrally or non-centrally within the bandage. A cast formed from a tubular bandage with similar substrate layers and a central opening may have a uniform weight per unit area of hardenable resin on substrate layers surrounding a body portion which is approximately 50% or less than 50% (when the tube is extended) of the total weight per unit area of resin in the bandage. Similarly a cast formed from a bandage with a non-central opening may have weight per unit area of hardenable resin on substrate layers on one side of the body portion which is greater than that on the other side thereof. Casts with a non-uniform weight per unit area of resin can also be formed from a bandage having substrate layers of different weight or thickness on either side of a tubular opening.

In a further aspect the present invention provides a method of forming a tubular bandage of the invention which comprises superposing a plurality of elongate layers including substrate layers capable of carrying a hardenable resin and joining each layer to an adjacent layer at the longitudinal side regions thereof.

The method of the invention thus avoids the need to assemble individual tubular layers by pulling one layer over or within another layer.

The layers can be joined by any suitable means including heat sealing, adhesive sealing and stitching.

In the method of the invention individual layers can be attached to an adjacent layer in successive operations. It is preferred, however, that all the layers are joined at a longitudinal region thereof in one operation, for example by stitching.

In favoured methods of the invention therefore the layers are joined by stitching.

In a favoured method of the invention the elongate layers including substrate layer and optionally padding layers and barrier layers can be assembled in superposed arrangement ie. a stack and then stitched by a conventional sewing method at the longitudinal side region thereof. In a preferred method the stitching is located near the two longitudinal side edges of the layers and preferably also encompasses the edges thereof to reduce the rigid stitched area which could project from the edge of a tubular bandage or cast of the invention in use. A favoured stitching comprises a zig-zag stitch in which every other stitch is missing and in which the missed stitch overlaps and encompasses the edge of the layers.

The tubular fabric of the invention can be impregnated or coated with a hardenable resin to form the tubular casting bandage of the invention.

Therefore in yet another aspect the invention provides a method of forming a tubular bandage of the invention which comprises impregnating or coating the tubular fabric of the invention with a hardenable resin.

The hardenable resin will normally be in a liquid state to facilitate the impregnation or coating process. Hardenable prepolymer resins for example polyurethane or acrylic prepolymer resins are preferably liquid at temperatures between 10° to 30° C. Solid or highly viscous prepolymers can be rendered liquid by any suitable method such as a hot melt or solvent method.

A tubular fabric of the invention can be coated or impregnated with liquid prepolymer by conventional methods such as a two roll nip coating or impregnating method. In such a method the tubular fabric is in the form of a stack of superposed layers.

This method of the invention avoids the necessity of having to coat or impregnate individual tubular layers and then assemble the coated tubular layers into a multilayer coating bandage.

The tubular fabric can be coated or impregnated in one or more passes until the requisite weight of resin has been deposited on the bandage. When the tubular fabric used in the method comprises a pair of padding layers it is preferred that the tubular fabric also comprises a pair of barrier layers to inhibit resin penetrating to the padding layers.

When the liquid prepolymer resin is a water hardenable resin it is desirable to dry the substrate for example by oven or vacuum drying prior to coating or impregnation to reduce the water content thereof to less than 1% by weight and preferably to less than 0.1% by weight.

A tubular casting bandage may have apertures provided by knitted or woven substrate layers.

The tubular casting bandage, however, may be provided with apertures or holes in addition to those provided by the interstices in the fabric forming the substrates to allow the hardened cast to be breathable. The holes need to be sufficiently large such that they do not fill up with resin when the substrate is impregnated or coated with the resins.

Aptly the area of each hole or aperture can be from 1 to 100 mm$^2$. Suitably the area of each tube will be not more than 15 mm$^2$ more suitably about 10 mm$^2$. The density of the holes or apertures will depend upon such factors as the required strength of the cast and the breathability required. Aptly the distribution will not be greater than about one per 50 cm$^2$.

The holes or apertures may be mechanically formed in the substrate prior to coating or impregnation of the resin. However, where knitted substrates are employed holes of a suitable size and distribution can be included within the knitting pattern of the knitted substrate.

The walls of orthopaedic casts formed from such bandages will preferably be porous to allow the transmission of moisture vapour. The walls of the cast may be provided with additional apertures or holes as hereinbefore mentioned to render the cast highly permeable to moisture vapour.

The tubular bandage of the invention can be adapted in size to the size of the body portion to be immobilised by the cast formed therefrom. The elastically extensible nature of tubular bandage can be adapted to allow the bandage to be applied over a body extremity to the body portion and to conform therewith.

Where the affected body portion is an ankle or a foot the tubular bandage may be in the shape of a sock optionally with its toe end removed. When the affected body potion is a wrist or hand the system may have a hole in a side portion thereof to accommodate a thumb region of the hand. The tubular bandage may be an individual tube or part of a connected series of tubes, for example in the form of a continuous length of a tube from which individual tubes may be cut.

The bandage may be packaged within a pouch. When the resin is water activatable, a foil pack may be employed which is impermeable to both liquid water and water vapour to inhibit premature hardening of the resin of the bandage. For light activated resins, the bandage may be packaged in an opaque pouch.

The bandage may be packaged as a flattened, folded or concertinered tube and may have a suitable interliner to prevent adjacent portions of the inner surface of the tube from contacting each other. In an alternative arrangement the tube may be rolled up to form a "doughnut", preferably with an interliner separating adjacent surfaces of the rolled tube. Suitable interliners may be formed from wax-coated or siliconised papers and the like.

In order to assist application of the tubular system or unrolling of a prepackaged tubular system, slip agents may be incorporated into the resin or applied to the surface of the resin coated substrate. Suitable slip agents include silicones, surfactants and the like.

The tubular bandage may be sterile within a bacteria-proof pack. The system be rendered sterile within the pack by a conventional sterilisation method such as gamma irradiation.

The tubular bandage of the invention can be applied to a body portion to form a cast thereon. Thus in another aspect the invention provides a method of forming a cast on a body portion by applying thereto a tubular casting bandage of the invention.

The bandage can be applied to a body portion by means of tubular opening or region of the bandage which is preferably defined by a pair of padding layers.

A tubular bandage of the invention, however, which does not comprise padding layers can be applied of a body portion previously covered by a padding layer for example a tubular padding disclosed in United Kingdom Patent Application No. 2221651.

The extensible nature of the substrate layers other layers thereon allows the bandage to be applied to a body portion via a body limb extremity. Manual application of the bandage can be assisted by pre-rolling the bandage into a "doughnut" shape or torus. The bandage, however, may conveniently be applied to the body portion by means of an applicator. The applicator can be a conventional expandible cylindrical shaped applicator of the type used for the application of tubular bandages.

The bandage for a hand or lower arm can be provided with a side hole inward of one end thereof prior to or after application to accommodate a thumb region of the hand.

After the bandage has been applied to the body portion, the hardenable resin can be hardened, for example by actinic (ultra-violet or visible light) radiation or by contact with water or moisture to form a cast about the body portion. The bandage, however, can be contacted with water or with moisture vapour prior to application thereof providing that the bandage is in its pre-hardened flexible and extensible state during application.

The applied tubular casting bandage of the invention after hardening of the resin forms a orthopaedic cast about a body portion.

In yet another aspect the present invention provides an orthopaedic cast formed from the tubular casting bandage of the invention.

The cast of the invention comprises a plurality of substrate layers which can advantageously provide the cast with a improved cast strength over a cast with a single substrate layers.

Furthermore, the cast of the invention can be adapted to provide a substantially uniform or non-uniform thickness or weight per unit area of the cast about the body portion according to the type and degree of support or immobilising required.

The invention will now be illustrated by way of example only, with reference to the following drawings.

Figure 1:
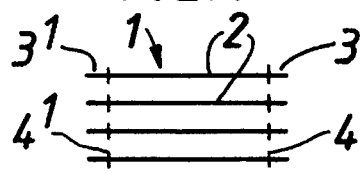
FIG. 1 is a schematic view of one embodiment of the invention.
Figure 1A:
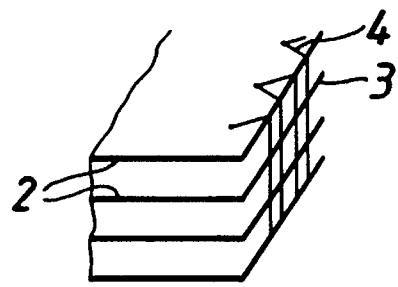
FIG. 1a is an enlarged diagrammatic perspective view of a side edge region of the embodiment of FIG. 1.

FIG. 1 shows a casting bandage (1) of the invention which comprises a stack of four single elongate extensible substrate layers (2) carrying a hardenable resin. The layers are joined together at their longitudinal side edge regions (3, 3$^1$) by stitches (4, 4$^1$). An enlarged view of stitches (4) at one set of edge regions (3) of bandage (1) is shown in FIG. 1A. Stitches (4) are zig-zag stitches which are missing at edge region (3) so that they can interlock and bind or encompass at these edge regions (3). The joined adjacent substrate layers (2) thus provide the casting bandage (1) with three tubular regions which are adapted to be placed over a body portion such as a limb extremity.

Figure 2:
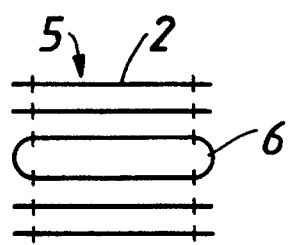
FIG. 2 is an expanded view of a side edge of FIG. 1.

FIG. 2 shows a bandage (5) similar to that of FIG. 1 which includes a tubular padding layer (6) centrally located within the substrate layers (2).

Figure 3:
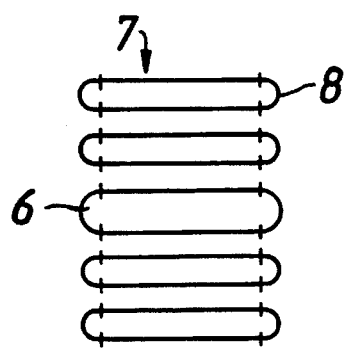
FIGS. 3 to 6 are schematic views of further embodiments of the invention.

FIG. 3 shows a bandage (7) similar to that of FIG. 3 which has tubular substrate layers (8) instead of single layers to provide the bandage (7) with eight substrate layers.

Figure 4:
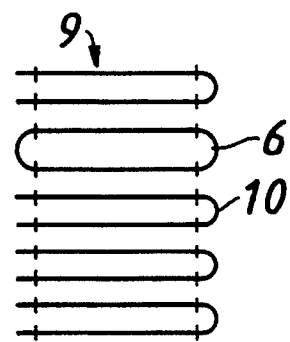

FIG. 4 shows a bandage (9) similar to that of FIG. 3 which has folded substrate layers (10) instead of tubular layers and tubular padding layer (6) is located non-symmetrically ie. to one side of the bandage (9).

Figure 5:
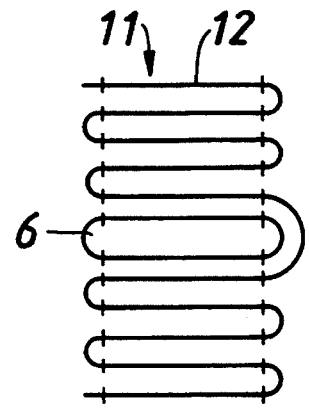

FIG. 5 show a bandge (11) similar to that of FIG. 3 which has folded substrate layers (12) formed from a single length.

Figure 6:
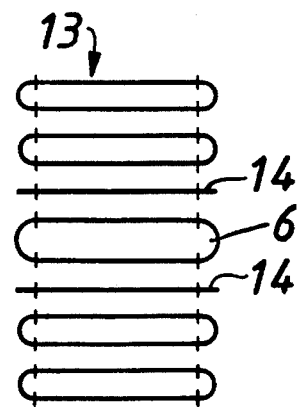

FIG. 6 shows a bandage (13) similar to that of FIG. 3 which has liquid impermeable barrier layers (14) located either side of the central tubular padding layer.

The invention will now be illustrated by reference to the following example:

EXAMPLE

Preparation of Substrate

Four elastic stockinette tubes (length 330 mm lay flat width 88 mm) were arranged in a stack to give a substrate with eight layers. The stockinette used was a rib knitted (1×1) fabric containing 2×167 decitex twisted polyester yarns and 50's rubber filament laid in spirally within the knitted yarns.

The stacked layers were then stitched at both edges with a zig-zag stitch with every other stitch missing at the edges so that these stitches encompassed or bound the edges of the substrate.

The substrate had a weight per unit area of 3023 gm$^{-2}$.

The substrate before being coated was dried in a vacuum oven at 60° C. for 24 hours and packed in a waterproof foil pack.

Preparation of Casting Bandage

The substrate prepared above was coated with a water hardenable coating resin using a conventional two roll nip impregnation apparatus in which resin was applied to both sides of the substrate in the nip. This process was repeated several times until the coated substrate contained 61.5% by weight of resin (4819 gm²).

The coated substrate was then cut into suitable lengths (0.3 meter) for forming tubular arm casting bandages. The casting bandages were then individually packed in a sealed foil pouch.

The resin used in this example was the polyurethane disclosed in Example 4 of WO9014060.

We claim:

1. A tubular orthopaedic casting bandage comprising a stack formed of a plurality of layers of hardenable casting material, having first and second opposed longitudinal side edges, said stack comprising at least one folded sheet member, said folded sheet member forming two layers in said stack, said layers being joined together at said first and second opposed longitudinal side edges thereof by zig-zag joining means, two adjacent layers of the stack defining a sleeve for receiving a body member.

2. A bandage according to claim 1 further comprising a padding member secured between adjacent layers of the stack.

3. A tubular orthopaedic casting bandage comprising a stack formed of a plurality of layers of hardenable casting material, having first and second opposed longitudinal side edges, which are joined together by said first and second opposed longitudinal side edges thereof by zig-zag joining means, two adjacent layers of the stack defining a sleeve for receiving a body member, said bandage further comprising a padding member secured between adjacent layers of the stack.

4. A tubular orthopaedic casting bandage comprising a stack formed of a plurality of layers of hardenable casting material, having first and second opposed longitudinal side edges, which are joined together by said first and second opposed longitudinal side edges thereof by zig-zag joining means, two adjacent layers of the stack defining a sleeve for receiving a body member, said zig-zag joining means comprising missing regions which overlap and encompass each of said side edges.

5. A tubular orthopaedic casting bandage comprising a stack formed of a plurality of layers of hardenable casting material, having first and second opposed longitudinal side edges, which are joined together by said first and second opposed longitudinal side edges thereof by zig-zag joining means, two adjacent layers of the stack defining a sleeve for receiving a body member, said zig-zag joining means comprising zig-zag stitching having missed stitches which overlap and encompass each of said side edges.

6. A bandage according to claim 1, 3, 4 or 5 wherein the stack further comprises at least one tubular member, each tubular member forming two layers in said stack.

7. A bandage according to claim 1, 3, 4 or 5 wherein the stack further comprises at least one sheet member, each sheet member forming one layer in said stack.

8. A bandage according to claim 1, 3, 4 or 5 wherein the stack further comprises one or more tubular members and one or more sheet members, each tubular member forming two layers in said stack and each sheet member forming one layer in said stack.

9. A bandage according to claim 1, 3, 4 or 5 further comprising a moisture vapour permeable liquid water impermeable barrier secured between adjacent layers of the stack.

10. A bandage according to claim 1, 3, 4 or 5 wherein said zig-zag joining means comprises zig-zag stitching.

11. A bandage according to claim 1, 3, 4, or 5 wherein the stack comprises at least four layers.

12. A tubular orthopaedic cast formed by hardening a hardenable casting material applied to a casting bandage according to claim 1, 3, 4 or 5.

13. A method of forming a tubular cast on a body member of a patent comprising placing a bandage according to claim 1, 3, 4 or 5 on said body member and hardening the hardenable casting material.

14. A casting bandage according to claim 1 or 3 wherein said zig-zag joining means comprises missing regions which overlap and encompass each of said side edges.

15. A casting bandage according to claim 1, 3 or 4 wherein said zig-zag joining means comprises zig-zag stitching having missed stitches which overlap and encompass each of said side edges.

16. A casting bandage according to claim 15 which is extensible in the longitudinal direction.

17. A casting bandage according to claim 16 wherein said bandage is extensible in a direction transverse to the longitudinal direction.

18. A method for forming a tubular orthopaedic casting bandage comprising a stack formed of a plurality of layers of hardenable casting material which are joined together at first and second opposed longitudinal side edges thereof by zig-zag stitching, two adjacent layers of the stack defining a sleeve for receiving a body member, said method comprising forming a stack of layers of bandage material, having side edges and stitching the side edges of the stack with zig-zag stitching, wherein said zig-zag stitching includes missed stitches which overlap and encompass said side edges.

19. A method according to claim 18 further comprising the step of impregnating or coating at least part of the bandage with an hardenable casting material.

20. A method according to claim 18 wherein the stack comprises a plurality of tubular members, each tubular member forming adjacent layers in said stack.

21. A method according to claim 18 wherein said fabric is extensible in the longitudinal direction.

22. A method according to claim 21 wherein said fabric is extensible in a direction transverse to the longitudinal direction.

* * * * *